(12) United States Patent
Malinowski (10) Patent No.: US 11,013,913 B2
(45) Date of Patent: May 25, 2021

(54) KITS AND METHODS FOR SECURING A BURR HOLE PLUGS FOR STIMULATION SYSTEMS

(71) Applicant: Boston Scientific Neuromodulation Corporation, Valencia, CA (US)

(72) Inventor: Zdzislaw Bernard Malinowski, Castaic, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 293 days.

(21) Appl. No.: 16/351,350

(22) Filed: Mar. 12, 2019

(65) Prior Publication Data

US 2019/0282802 A1    Sep. 19, 2019

Related U.S. Application Data

(60) Provisional application No. 62/643,964, filed on Mar. 16, 2018.

(51) Int. Cl.
*A61N 1/05* (2006.01)
*A61B 17/16* (2006.01)
(Continued)

(52) U.S. Cl.
CPC ........ *A61N 1/0539* (2013.01); *A61B 17/1615* (2013.01); *A61B 17/1739* (2013.01);
(Continued)

(58) Field of Classification Search
CPC ............ A61B 17/1615; A61B 17/1739; A61B 2090/103; A61B 5/6864; A61B 90/11;
(Continued)

(56) References Cited

U.S. PATENT DOCUMENTS

| 979,652 A | 12/1910 | Church |
| 2,186,277 A | 1/1940 | Tetens |

(Continued)

FOREIGN PATENT DOCUMENTS

| EP | 0911061 | 4/1999 |
| JP | S55-112538 | 7/1980 |

(Continued)

OTHER PUBLICATIONS

Lieberman, Daniel E. et al., Basicranial influence on overall cranial shape, Journal of Human Evolution, vol. 38 (2000) pp. 291-315.
(Continued)

*Primary Examiner* — Kathleen S Holwerda
*Assistant Examiner* — Brooke Labranche
(74) *Attorney, Agent, or Firm* — Branch Partners PLLC; Bruce E. Black (57) ABSTRACT

A kit or arrangement for securing a burr hole plug that includes a guide base having an upper flange, a lower flange, and a connecting member coupling the upper flange to the lower flange, each of the upper flange and the lower flange defining one or more guide holes, wherein the one or more guide holes of the upper flange are aligned with the one or more guide holes of the lower flange; a drill shank including a cutting element and a main shaft that are configured to pass through any one of the one or more guide holes in the upper flange; and one or more guide collets including a collet shaft and a fastener tube extending from the collet shaft to receive a fastener, where the collet shaft and fastener tube are configured for insertion into any one of the guide holes in the upper flange.

20 Claims, 8 Drawing Sheets

(51) Int. Cl.
*A61B 17/17* (2006.01)
*A61B 90/11* (2016.01)
A61B 90/10 (2016.01)
A61N 1/36 (2006.01)
A61B 5/00 (2006.01)
A61F 2/28 (2006.01)
A61N 1/375 (2006.01)

(52) U.S. Cl.
CPC .............. *A61B 90/11* (2016.02); *A61B 5/6864* (2013.01); *A61B 2090/103* (2016.02); *A61F 2/2875* (2013.01); *A61N 1/0534* (2013.01); *A61N 1/3605* (2013.01); *A61N 1/375* (2013.01)

(58) Field of Classification Search
CPC ... A61B 90/10; A61B 17/1617; A61F 2/2875; A61N 1/0534; A61N 1/0539; A61N 1/3605; A61N 1/375
See application file for complete search history.

(56) References Cited

U.S. PATENT DOCUMENTS

| | | |
|---|---|---|
| 2,521,301 A | 9/1950 | Morrison |
| 2,873,822 A | 2/1959 | Sloan |
| 2,912,712 A | 11/1959 | Shamban et al. |
| 3,758,827 A | 9/1973 | Schroder et al. |
| 3,826,952 A | 7/1974 | Iwasaki et al. |
| 3,829,737 A | 8/1974 | Johnsson |
| 4,114,603 A | 9/1978 | Wilkinson |
| 4,245,645 A | 1/1981 | Arseneault et al. |
| 4,297,609 A | 10/1981 | Hirao et al. |
| 4,315,180 A | 2/1982 | Kondo et al. |
| 4,328,313 A | 5/1982 | Simonson et al. |
| 4,328,813 A | 5/1982 | Ray |
| 4,467,800 A | 8/1984 | Zytkovicz |
| 4,741,571 A | 5/1988 | Godette |
| 4,805,634 A | 2/1989 | Ullrich et al. |
| 4,826,487 A | 5/1989 | Winter |
| 4,850,359 A | 7/1989 | Putz |
| 4,931,056 A | 6/1990 | Ghajar et al. |
| 4,955,891 A | 9/1990 | Carol |
| 4,998,938 A | 3/1991 | Ghajar et al. |
| 5,116,345 A | 5/1992 | Jewell et al. |
| 5,193,539 A | 3/1993 | Schulman et al. |
| 5,193,540 A | 3/1993 | Schulman et al. |
| 5,201,737 A | 4/1993 | Leibinger et al. |
| 5,235,990 A | 8/1993 | Dempsey |
| 5,300,080 A | 4/1994 | Clayman et al. |
| 5,324,316 A | 6/1994 | Schulman et al. |
| 5,330,485 A | 7/1994 | Clayman et al. |
| 5,464,446 A | 11/1995 | Dreessen et al. |
| 5,484,445 A | 1/1996 | Knuth |
| 5,496,356 A | 3/1996 | Hudz |
| 5,503,164 A | 4/1996 | Friedman |
| 5,549,620 A | 8/1996 | Bremer |
| 5,707,373 A | 1/1998 | Sevrain et al. |
| 5,732,699 A | 3/1998 | Lundback |
| 5,776,144 A | 7/1998 | Levsieffer et al. |
| 5,800,504 A | 9/1998 | Bellifemine |
| 5,843,150 A | 12/1998 | Dreessen et al. |
| 5,865,842 A | 2/1999 | Knuth et al. |
| 5,891,028 A | 4/1999 | Lundback |
| 5,897,531 A | 4/1999 | Amirana |
| 5,916,154 A | 6/1999 | Hobbs et al. |
| 5,927,277 A | 7/1999 | Baudino et al. |
| 5,954,687 A | 9/1999 | Baudino |
| 5,984,930 A | 11/1999 | Maciunas et al. |
| 5,993,463 A | 11/1999 | Truwit |
| 6,006,124 A | 12/1999 | Fischell et al. |
| 6,016,449 A | 1/2000 | Fischell et al. |
| 6,044,304 A | 3/2000 | Baudino |
| 6,050,098 A | 4/2000 | Meyer et al. |
| 6,050,998 A | 4/2000 | Fletcher |
| 6,073,048 A | 6/2000 | Kieval et al. |
| 6,094,598 A | 7/2000 | Elsberry et al. |
| 6,117,143 A | 9/2000 | Hynes et al. |
| 6,126,663 A | 10/2000 | Hair |
| 6,128,537 A | 10/2000 | Rise |
| 6,128,538 A | 10/2000 | Fischell et al. |
| 6,134,474 A | 10/2000 | Fischell et al. |
| 6,134,477 A | 10/2000 | Knuteson |
| 6,171,239 B1 | 1/2001 | Humphrey |
| 6,181,969 B1 | 1/2001 | Gord |
| 16,175,710 | 1/2001 | Kamaji et al. |
| 6,200,329 B1 | 3/2001 | Fung et al. |
| 6,210,417 B1 | 4/2001 | Baudino et al. |
| 6,224,450 B1 | 5/2001 | Norton |
| 6,230,049 B1 | 5/2001 | Fischell et al. |
| 6,269,270 B1 | 7/2001 | Boveja |
| 6,271,094 B1 | 8/2001 | Boyd et al. |
| 6,284,729 B1 | 9/2001 | Bernfield et al. |
| 6,295,944 B1 | 10/2001 | Lovett |
| 6,321,104 B1 | 11/2001 | Gielen et al. |
| 6,324,433 B1 | 11/2001 | Errico |
| 6,353,762 B1 | 3/2002 | Baudino et al. |
| 6,354,299 B1 | 3/2002 | Fischell et al. |
| 6,356,729 B1 | 3/2002 | Sasaki et al. |
| 6,356,777 B1 | 3/2002 | Garfield et al. |
| 6,356,792 B1 | 3/2002 | Errico |
| 6,364,278 B1 | 4/2002 | Lin et al. |
| 6,374,140 B1 | 4/2002 | Rise |
| 6,391,985 B1 | 5/2002 | Goode et al. |
| 6,413,263 B1 | 7/2002 | Lobdill et al. |
| 6,427,086 B1 | 7/2002 | Fischell et al. |
| 6,447,443 B1 | 9/2002 | Keogh et al. |
| 6,459,936 B2 | 10/2002 | Fischell et al. |
| 6,463,328 B1 | 10/2002 | John |
| 6,464,687 B1 | 10/2002 | Ishikawa et al. |
| 6,466,822 B1 | 10/2002 | Pless |
| 6,480,743 B1 | 11/2002 | Kirkpatrick et al. |
| 6,482,182 B1 | 11/2002 | Carroll et al. |
| 6,516,227 B1 | 2/2003 | Meadows |
| 6,560,486 B1 | 5/2003 | Osorio et al. |
| 6,571,127 B1 | 5/2003 | Ben-Haim et al. |
| 6,574,498 B1 | 6/2003 | Gilboa |
| 6,597,954 B1 | 7/2003 | Pless et al. |
| 6,609,020 B2 | 8/2003 | Gill |
| 6,609,029 B1 | 8/2003 | Mann et al. |
| 6,609,032 B1 | 8/2003 | Woods et al. |
| 6,618,623 B1 | 9/2003 | Pless et al. |
| 6,647,296 B2 | 11/2003 | Fischell et al. |
| 6,690,974 B2 | 2/2004 | Archer et al. |
| 6,741,892 B1 | 5/2004 | Meadows et al. |
| 6,795,737 B2 | 9/2004 | Gielen et al. |
| 6,845,257 B2 | 1/2005 | Fuimaono et al. |
| 6,845,267 B2 | 1/2005 | Harrison et al. |
| 6,895,280 B2 | 5/2005 | Meadows et al. |
| 6,920,359 B2 | 7/2005 | Meadows et al. |
| 6,944,501 B1 | 9/2005 | Pless |
| 6,950,707 B2 | 9/2005 | Whitehurst |
| 7,004,948 B1 | 2/2006 | Pianca et al. |
| 7,033,326 B1 | 4/2006 | Pianca et al. |
| 7,050,855 B2 | 5/2006 | Zeijlemaker et al. |
| 7,090,661 B2 | 8/2006 | Morris et al. |
| 7,118,828 B2 | 10/2006 | Dodd et al. |
| 7,146,222 B2 | 12/2006 | Boling |
| 7,174,213 B2 | 2/2007 | Pless |
| 7,174,219 B2 | 2/2007 | Wahlstrand et al. |
| 7,177,701 B1 | 2/2007 | Pianca |
| 7,204,840 B2 | 4/2007 | Skakoon et al. |
| 7,212,864 B2 | 5/2007 | Wahlstrand et al. |
| 7,235,084 B2 | 6/2007 | Skakoon et al. |
| 7,242,982 B2 | 7/2007 | Singhal et al. |
| 7,244,150 B1 | 7/2007 | Brase et al. |
| 7,343,205 B1 | 3/2008 | Pianca et al. |
| 7,369,899 B2 | 5/2008 | Malinowski et al. |
| 7,421,297 B2 | 9/2008 | Gifakis et al. |
| 7,437,193 B2 | 10/2008 | Parramon et al. |
| 7,450,997 B1 | 11/2008 | Pianca et al. |
| 7,454,251 B2 | 11/2008 | Rezai et al. |
| 7,479,146 B2 | 1/2009 | Malinowski et al. |
| 7,548,775 B2 | 6/2009 | Kipke et al. |

(56) References Cited

U.S. PATENT DOCUMENTS

| | | |
|---|---|---|
| 7,636,596 B2 | 12/2009 | Solar |
| 7,672,734 B2 | 3/2010 | Anderson et al. |
| 7,682,745 B2 | 3/2010 | Howard et al. |
| 7,756,922 B2 | 7/2010 | Basu et al. |
| 7,761,165 B1 | 7/2010 | He et al. |
| 7,766,922 B1 | 8/2010 | Daglow et al. |
| 7,783,359 B2 | 8/2010 | Meadows |
| 7,787,945 B2 | 8/2010 | Greene |
| 7,792,590 B1 | 9/2010 | Pianca et al. |
| 7,809,446 B2 | 10/2010 | Meadows |
| 7,815,651 B2 | 10/2010 | Skakoon et al. |
| 7,833,231 B2 | 11/2010 | Skakoon et al. |
| 7,833,253 B2 | 11/2010 | Ralph et al. |
| 7,949,395 B2 | 5/2011 | Kuzma |
| 7,949,410 B2 | 5/2011 | Rodriguez |
| 7,974,706 B2 | 7/2011 | Moffitt et al. |
| 7,981,119 B2 | 7/2011 | Lando et al. |
| 8,024,045 B2 | 9/2011 | Carlton et al. |
| 8,043,304 B2 | 10/2011 | Barker |
| 8,137,362 B2 | 3/2012 | Malinowski |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,313,453 B2 | 11/2012 | Carbunaru et al. |
| 8,364,278 B2 | 1/2013 | Pianca et al. |
| 8,391,985 B2 | 3/2013 | McDonald |
| 8,397,732 B2 | 3/2013 | Singhal et al. |
| 8,425,534 B2 | 4/2013 | Barker |
| 8,473,061 B2 | 6/2013 | Moffitt et al. |
| 8,571,664 B2 | 10/2013 | Anderson et al. |
| 8,571,665 B2 | 10/2013 | Moffitt et al. |
| 8,688,235 B1 | 4/2014 | Pianca et al. |
| 8,731,686 B2 | 5/2014 | Lane et al. |
| 8,764,767 B2 | 7/2014 | Barker |
| 8,792,993 B2 | 7/2014 | Pianca et al. |
| 8,812,133 B2 | 8/2014 | Funderburk |
| 9,043,000 B2 | 5/2015 | Lane et al. |
| 9,050,191 B2 | 6/2015 | Funderburk |
| 9,084,901 B2 | 7/2015 | Wahlstrand |
| 9,101,756 B1 | 8/2015 | Pianca et al. |
| 9,468,751 B2 | 10/2016 | Bonde |
| 9,474,896 B2 | 10/2016 | Lopez |
| 9,492,660 B2 | 11/2016 | Mouchawar et al. |
| 9,604,052 B2 | 3/2017 | Behymer et al. |
| 9,610,437 B2 | 4/2017 | Okun et al. |
| 10,232,169 B2 | 3/2019 | Govea et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0052610 A1 | 5/2002 | Skakoon et al. |
| 2002/0072770 A1 | 6/2002 | Pless |
| 2002/0077670 A1 | 6/2002 | Archer et al. |
| 2002/0099412 A1 | 7/2002 | Fischell et al. |
| 2002/0156372 A1 | 10/2002 | Skakoon et al. |
| 2002/0169485 A1 | 11/2002 | Pless et al. |
| 2003/0028199 A1 | 2/2003 | Ghahremani et al. |
| 2003/0083724 A1 | 5/2003 | Jog et al. |
| 2003/0088274 A1 | 5/2003 | Gliner et al. |
| 2003/0088303 A1 | 5/2003 | Goode |
| 2004/0034367 A1 | 2/2004 | Malinowski |
| 2004/0122446 A1 | 6/2004 | Solar |
| 2004/0153129 A1 | 8/2004 | Pless et al. |
| 2004/0176673 A1 | 9/2004 | Wahlstrand et al. |
| 2005/0003268 A1 | 1/2005 | Scott et al. |
| 2005/0004618 A1 | 1/2005 | Scott et al. |
| 2005/0010261 A1 | 1/2005 | Luders et al. |
| 2005/0015128 A1 | 1/2005 | Rezai et al. |
| 2005/0049646 A1 | 3/2005 | Luders et al. |
| 2005/0070458 A1 | 3/2005 | John |
| 2005/0075679 A1 | 4/2005 | Gliner et al. |
| 2005/0075680 A1 | 4/2005 | Lowry et al. |
| 2005/0092707 A1 | 5/2005 | Chantalat |
| 2005/0107753 A1 | 5/2005 | Rezai et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0222641 A1 | 10/2005 | Pless |
| 2005/0228249 A1 | 10/2005 | Boling |
| 2006/0129204 A1 | 6/2006 | Pless et al. |
| 2006/0190054 A1 | 8/2006 | Malinowski et al. |
| 2006/0190055 A1 | 8/2006 | Malinowski et al. |
| 2006/0212093 A1 | 9/2006 | Pless et al. |
| 2006/0224216 A1 | 10/2006 | Pless et al. |
| 2006/0229686 A1 | 10/2006 | Giftakis et al. |
| 2006/0247684 A1 | 11/2006 | Halperin et al. |
| 2007/0106143 A1 | 5/2007 | Flaherty |
| 2007/0150036 A1 | 6/2007 | Anderson |
| 2007/0173844 A1 | 7/2007 | Ralph et al. |
| 2007/0208352 A1 | 9/2007 | Henderson et al. |
| 2007/0225773 A1 | 9/2007 | Shen et al. |
| 2007/0233158 A1 | 10/2007 | Rodriguez |
| 2007/0265683 A1 | 11/2007 | Ehrlich |
| 2008/0071313 A1 | 3/2008 | Stevenson et al. |
| 2008/0100061 A1 | 5/2008 | Sage et al. |
| 2008/0172068 A1 | 7/2008 | Adams et al. |
| 2008/0243219 A1 | 10/2008 | Malinowski et al. |
| 2008/0275466 A1 | 11/2008 | Skakoon |
| 2009/0112327 A1 | 4/2009 | Lane et al. |
| 2009/0118804 A1 | 5/2009 | Moffitt et al. |
| 2009/0157157 A1 | 6/2009 | Schorn et al. |
| 2009/0182351 A1 | 7/2009 | Malinowski et al. |
| 2009/0187149 A1 | 7/2009 | Nelson |
| 2009/0187222 A1 | 7/2009 | Barker |
| 2009/0202899 A1 | 8/2009 | Pyszczek |
| 2009/0276021 A1 | 11/2009 | Meadows et al. |
| 2010/0023020 A1 | 1/2010 | Barker et al. |
| 2010/0023100 A1 | 1/2010 | Barker |
| 2010/0076535 A1 | 3/2010 | Pianca et al. |
| 2010/0114249 A1 | 5/2010 | Wahlstrand et al. |
| 2010/0145357 A1 | 6/2010 | Lane et al. |
| 2010/0268298 A1 | 10/2010 | Moffitt et al. |
| 2010/0280585 A1 | 11/2010 | Appenrodt et al. |
| 2010/0312193 A1 | 12/2010 | Stratton et al. |
| 2011/0004267 A1 | 1/2011 | Meadows |
| 2011/0005069 A1 | 1/2011 | Pianca |
| 2011/0054563 A1 | 3/2011 | Janzig et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2012/0316628 A1 | 12/2012 | Lopez |
| 2013/0006410 A1 | 1/2013 | Gentile et al. |
| 2013/0066410 A1* | 3/2013 | Funderburk .......... A61F 2/2875 607/116 |
| 2013/0066430 A1 | 3/2013 | Funderburk |
| 2013/0066431 A1 | 3/2013 | Funderburk |
| 2013/0105071 A1 | 5/2013 | Digiore et al. |
| 2013/0197424 A1 | 8/2013 | Bedenbaugh |
| 2013/0197602 A1 | 8/2013 | Pianca et al. |
| 2013/0304216 A1 | 11/2013 | Paspa et al. |
| 2014/0039587 A1 | 2/2014 | Romero |
| 2014/0257325 A1 | 9/2014 | Chavez et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |

(56) References Cited

U.S. PATENT DOCUMENTS

| | | |
|---|---|---|
| 2015/0045864 A1 | 2/2015 | Howard |
| 2015/0051681 A1 | 2/2015 | Hershey |
| 2015/0066120 A1 | 3/2015 | Govea |
| 2015/0151113 A1 | 6/2015 | Govea et al. |
| 2016/0089190 A1* | 3/2016 | Taber .............. A61B 17/1615 606/71 |
| 2016/0228692 A1 | 8/2016 | Steinke et al. |
| 2019/0143125 A1 | 5/2019 | Funderburk et al. |

FOREIGN PATENT DOCUMENTS

| | | |
|---|---|---|
| WO | 1998008554 | 3/1998 |
| WO | 1999055408 | 11/1999 |
| WO | 2000013743 | 3/2000 |
| WO | 20020045795 | 6/2002 |
| WO | 2003026738 | 4/2003 |
| WO | 20030028521 | 4/2003 |
| WO | 20040084749 | 10/2004 |
| WO | 2004105640 | 12/2004 |
| WO | 2005079903 | 9/2005 |
| WO | 2006031317 | 3/2006 |
| WO | 2008054691 | 5/2008 |
| WO | 2008054699 | 5/2008 |
| WO | 2008107815 | 9/2008 |
| WO | 2008107822 | 9/2008 |
| WO | 2008134509 | 11/2008 |
| WO | 2009055746 | 4/2009 |

OTHER PUBLICATIONS

Roberts DW, Hartov A. Kennedy FE, Miga MI, Paulsen KD: Intraoperative brain shift and deformation: A quantitative analysis of cortical displacement in 28 cases. Neurosurgery 43:749-760, 1998.

Dickhaus H., Ganser KA, Stuabert A., Bonsanto MM, Wirtz CR, Tronnier VM, Kunze S: Quantification of brain shift effects by MR-imaging. Engineering in Medicine and Biology Society vol. 2: 491-494, 1997.

Nimsky C., Gansland O., Cerny S., Hastreiter P., Greiner G., Fahlbusch R.: Quantification of, visualization of, and compensation for brain shift using intraoperative magnetic resonance imaging. Neurosurgery 47, 1070-1080, 2000.

Winkler D., Tittgemeyer M., Schwartz J., Preul C., Strecker K., Meixensberger J.: The first evaluation of brain shift during functional neurosurgery by deformation field analysis. Journal of Neurology, Neurosurgery, and Psychiatry 76 (8): 1161-3, 2005.

Axelsson, Stefan et al., Longitudinal cephalometric standards for the neurocranium in Norwegians from 6 to 21 years of age, European Journal of Orthodontics, vol. 25 (2003) pp. 185-198.

International Search Report and Written Opinion for PCT Application No. PCT/US2019/021920 dated Jun. 5, 2019.

\* cited by examiner

KITS AND METHODS FOR SECURING A BURR HOLE PLUGS FOR STIMULATION SYSTEMS

CROSS-REFERENCE TO RELATED APPLICATIONS

This application claims the benefit under 35 U.S.C. § 119(e) of U.S. Provisional Patent Application Ser. No. 62/643,964, filed Mar. 16, 2018, which is incorporated herein by reference.

FIELD

The present disclosure is directed to the area of burr hole plugs and kits and methods for securing burr hole plugs. The present disclosure is also directed to implantable electrical stimulation systems including the kits for securing burr hole plugs, as well as methods of making and using the kits, burr hole plugs, and electrical stimulation systems.

BACKGROUND

Implantable electrical stimulation systems have proven therapeutic in a variety of diseases and disorders. For example, stimulation of the brain, such as deep brain stimulation, can be used to treat a variety of diseases or disorders and spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the brain, nerves, or other tissue to be stimulated. The pulse generator in the control module generates electrical pulses that are delivered by the electrodes to body tissue.

BRIEF SUMMARY

In some aspects, a kit or arrangement for securing a burr hole plug includes a guide base including an upper flange, a lower flange, and a connecting member coupling the upper flange to the lower flange, each of the upper flange and the lower flange defining one or more guide holes, wherein the one or more guide holes of the upper flange are aligned with the one or more guide holes of the lower flange; a drill shank coupleable to a drill and including a cutting element and a main shaft that are configured to pass through any one of the one or more guide holes in the upper flange of the guide base; and one or more guide collets including a collet shaft and a fastener tube extending from the collet shaft to receive a fastener, where the collet shaft and fastener tube are configured for insertion into any one of the one or more guide holes in the upper flange of the guide base.

In at least some aspects, each of the upper flange and the lower flange defines at least two of the guide holes. In at least some aspects, the shaft of the drill shank has an outer diameter that is greater than an inner diameter of any one of the one or more guide holes in the lower flange of the guide base. In at least some aspects, each of the one or more guide holes in the lower flange has a diameter that decreases toward a bottom of the lower flange, where the shaft of the drill shank has an outer diameter that is greater than an inner diameter of at least a portion of any one of the one or more guide holes in the lower flange of the guide base.

In at least some aspects, the guide collet includes a collet flange disposed on the collet shaft opposite the fastener tube. In at least some aspects, the guide collet has an outer diameter larger than an inner diameter of any one of the one or more guide holes in the upper flange of the guide base.

In at least some aspects, the guide base further includes an alignment arrangement extending from the lower flange to align a base of the burr hole plug with the guide holes of the upper and lower flanges. In at least some aspects, the alignment arrangement includes one or more sections of a ring that fit within an opening of the base of the burr hole plug. In at least some aspects, the one or more sections of the ring form a compression or friction fit with the base of the burr hole plug. In at least some aspects, the alignment arrangement includes one or more pins for engaging the base of the burr hole plug. In at least some aspects, the kit further includes the base of the burr hole plug.

In at least some aspects, the kit further includes one or more fasteners disposed with each fastener disposed in the fastener tube of one of the one or more guide collets. In at least some aspects, the kit further includes the burr hole plug. In at least some aspects, the base defines a gap in at least the lower flange for positioning of a lead extending from a burr hole. In at least some aspects, the base further defines the gap in the upper flange and the connecting member.

In some aspects, a method of securing a burr hole plug to a patient using any of the kits described above includes aligning the guide base with a base of a burr hole plug on a skull of a patient, wherein the one or more guide holes of the upper and lower flanges are aligned with fastener openings in the base of the burr hole plug; drilling one or more pilot holes in the skull using the drill shank inserted into the one or more guide holes of the guide base; inserting the one or more guide collets into the guide holes of the guide base with a fastener in the fastener tube of each of the one or more guide collets; driving the one or more fasteners into the skull using the guide collets and the pilot holes; and removing the guide base leaving the base of the burr hole plug secured to the skull.

In at least some aspects, aligning the guide base includes engaging the base of the burr hole plug with an alignment arrangement extending from the lower flange of the guide base. In at least some aspects, engaging the base includes forming a compression or friction fit between the alignment arrangement of the guide base and the base of the burr hole plug. In at least some aspects, the alignment arrangement includes one or more pins and engaging the base includes engaging the base of the burr hole plug with the pins of the alignment arrangement of the guide base. In at least some aspects, aligning the guide base includes positioning a lead extending from a burr hole in a gap defined in at least the lower flange of the guide base.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of burr hole plugs and kits and methods for securing burr hole plugs. The present disclosure is also directed to implantable electrical stimulation systems including the kits for securing burr hole plugs, as well as methods of making and using the kits, burr hole plugs, and electrical stimulation systems.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that such leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
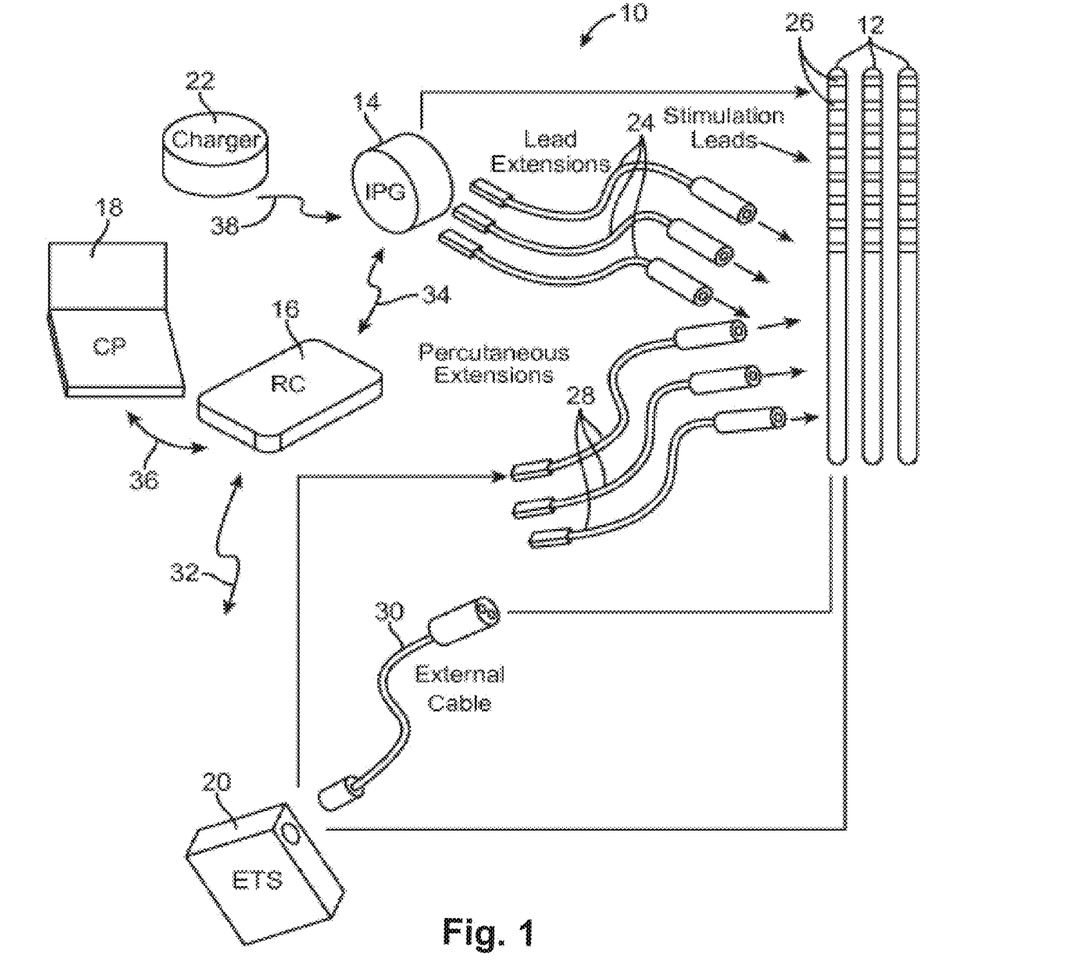
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
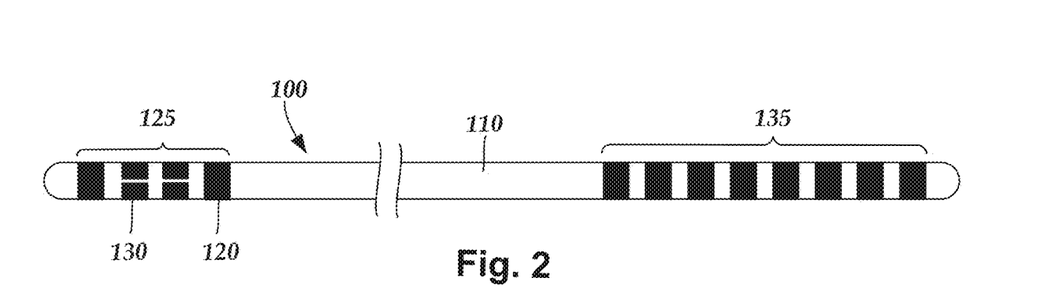
FIG. 2 is a schematic side view of one embodiment of an electrical stimulation lead.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads described herein include 8 electrodes. It will be understood that the leads could include any suitable number of electrodes. The leads can include ring electrodes, a distal-tip electrode, and/or one or more segmented electrodes in lieu of, or in addition to, one or more ring electrodes. Additionally, the term "elongated member" used herein includes leads (e.g., percutaneous, paddle, cuff, or the like), as well as intermediary devices (e.g., lead extensions, adaptors, splitters, or the like).

FIG. 2 illustrates one embodiment of a lead 100 with electrodes 125 disposed at least partially about a circumference of the lead 100 along a distal end portion of the lead and terminals 135 disposed along a proximal end portion of the lead 100. The lead 100 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of a stylet (not shown). The lead 100 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 100, advance the lead 100, retract the lead 100, or rotate the lead 100.

The lead 100 for deep brain stimulation can include stimulation electrodes, recording electrodes, or both. In at least some embodiments, the lead 100 is rotatable so that the stimulation electrodes can be aligned with the target neurons after the neurons have been located using the recording electrodes.

Stimulation electrodes may be disposed on the circumference of the lead 100 to stimulate the target neurons. Stimulation electrodes may be ring-shaped so that current projects from each electrode equally in every direction from the position of the electrode along a length of the lead 100. In the embodiment of FIG. 2, two of the electrodes 125 are ring electrodes 120. Ring electrodes 120 typically do not enable stimulus current to be directed from only a limited angular range around of the lead 100. Segmented electrodes 130, however, can be used to direct stimulus current to a selected angular range around the lead 100. When segmented electrodes 130 are used in conjunction with an implantable pulse generator that delivers constant current stimulus, current steering can be achieved to more precisely deliver the stimulus to a position around an axis of the lead 100 (i.e., radial positioning around the axis of the lead 100). To achieve current steering, segmented electrodes 130 can be utilized in addition to, or as an alternative to, ring electrodes 120.

As described above, the lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used (ON) or unused (OFF). When the electrode is used, the electrode can be used as an anode or cathode and carry anodic or cathodic current. In some instances, an electrode might be an anode for a period of time and a cathode for a period of time.

As described above, deep brain stimulation leads and other leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

Figure 3:
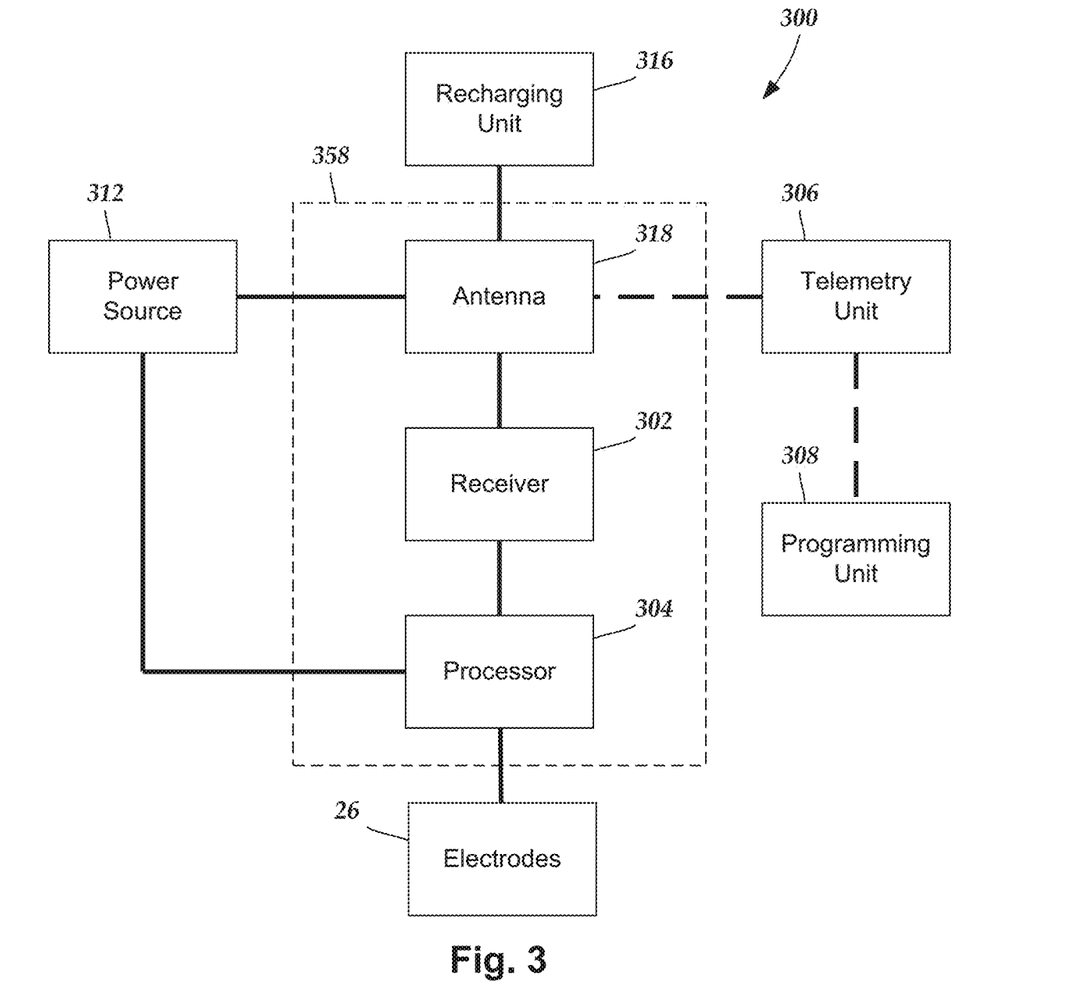
FIG. 3 is a schematic overview of one embodiment of components of a stimulation system, including an electronic subassembly disposed within a control module.

FIG. 3 is a schematic overview of one embodiment of components of an electrical stimulation system 300 including an electronic subassembly 358 disposed within a control module. The electronic subassembly 358 may include one or more components of the IPG. It will be understood that the electrical stimulation system can include more, fewer, or different components and can have a variety of different configurations including those configurations disclosed in the stimulator references cited herein.

Some of the components (for example, a power source 312, one or more antennas 318, a receiver 302, and a processor 304) of the electrical stimulation system can be positioned on one or more circuit boards or similar carriers within a sealed electronics housing of an implantable pulse generator (see e.g., 14 in FIG. 1), if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. In at least some embodiments, the antenna 318 (or the secondary antenna) is implemented using the auxiliary electrically-conductive conductor. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above. The electronic subassembly 358 and, optionally, the power source 312 can be disposed within a control module (e.g., the IPG 14 or the ETS 20 of FIG. 1).

In one embodiment, electrical stimulation signals are emitted by the electrodes (e.g., electrode array 26 in FIG. 1) to stimulate nerve fibers, muscle fibers, or other body tissues near the electrical stimulation system. The processor 304 is generally included to control the timing and electrical characteristics of the electrical stimulation system. For example, the processor 304 can, if desired, control one or more of the timing, frequency, strength, duration, and waveform of the pulses. In addition, the processor 304 can select which electrodes can be used to provide stimulation, if desired. In some embodiments, the processor 304 selects which electrode(s) are cathodes and which electrode(s) are anodes. In some embodiments, the processor 304 is used to identify which electrodes provide the most useful stimulation of the desired tissue.

Various processors can be used and may be an electronic device that, for example, produces pulses at a regular interval or the processor can be capable of receiving and interpreting instructions from an external programming unit 308 that, for example, allows modification of pulse characteristics. In the illustrated embodiment, the processor 304 is coupled to a receiver 302 which, in turn, is coupled to the optional antenna 318. This allows the processor 304 to receive instructions from an external source to, for example, direct the pulse characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the electrical stimulation system 300. The programming unit 308 can be part of the telemetry unit 306 or can provide signals or information to the telemetry unit 306 via a wireless or wired connection. One example of a suitable programming unit 308 is a computer operated by the user or clinician to send signals to the telemetry unit 306.

The signals sent to the processor 304 via the antenna 318 and the receiver 302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 300 to cease operation, to start operation, to start charging the battery, or to stop charging the battery. In other embodiments, the stimulation system does not include the antenna 318 or receiver 302 and the processor 304 operates as programmed.

Optionally, the electrical stimulation system 300 may include a transmitter (not shown) coupled to the processor 304 and the antenna 318 for transmitting signals back to the telemetry unit 306 or another unit capable of receiving the signals. For example, the electrical stimulation system 300 may transmit signals indicating whether the electrical stimulation system 300 is operating properly or not or indicating when the battery needs to be charged or the level of charge remaining in the battery. The processor 304 may also be capable of transmitting information about the pulse characteristics so that a user or clinician can determine or verify the characteristics.

In at least some instances of electrical stimulation of the brain, when a lead is implanted into the brain of a patient, the lead is inserted through a burr hole in the skull of the patient. The lead extends out of the burr hole and is coupled to a control module implanted elsewhere, for example, in the torso of the patient. A burr hole plug is provided in the burr hole to cover the opening through the skull, to protect the lead exiting the skull, and to firmly hold the lead in place to prevent or reduce lead migration within the brain.

At least some current burr hole plug placement methods provide little or no aid in controlling the placement, insertion, and fixation of mounting screws into the skull to hold the burr hole plug in place. The procedure of positioning and assuring secure fixation of the burr hole plug is often difficult due to the small size of the components, the hardness of the skull, and other factors. For example, it may be difficult to align the screws on the skull and insert the screws into the skull at the desired position for proper placement. Moreover, a screw head can be easily stripped, which may create sharp edges in the place of engagement with the screwdriver. This can may result in a future internal hemorrhage or skin erosion.

Figures 4A, 4B:
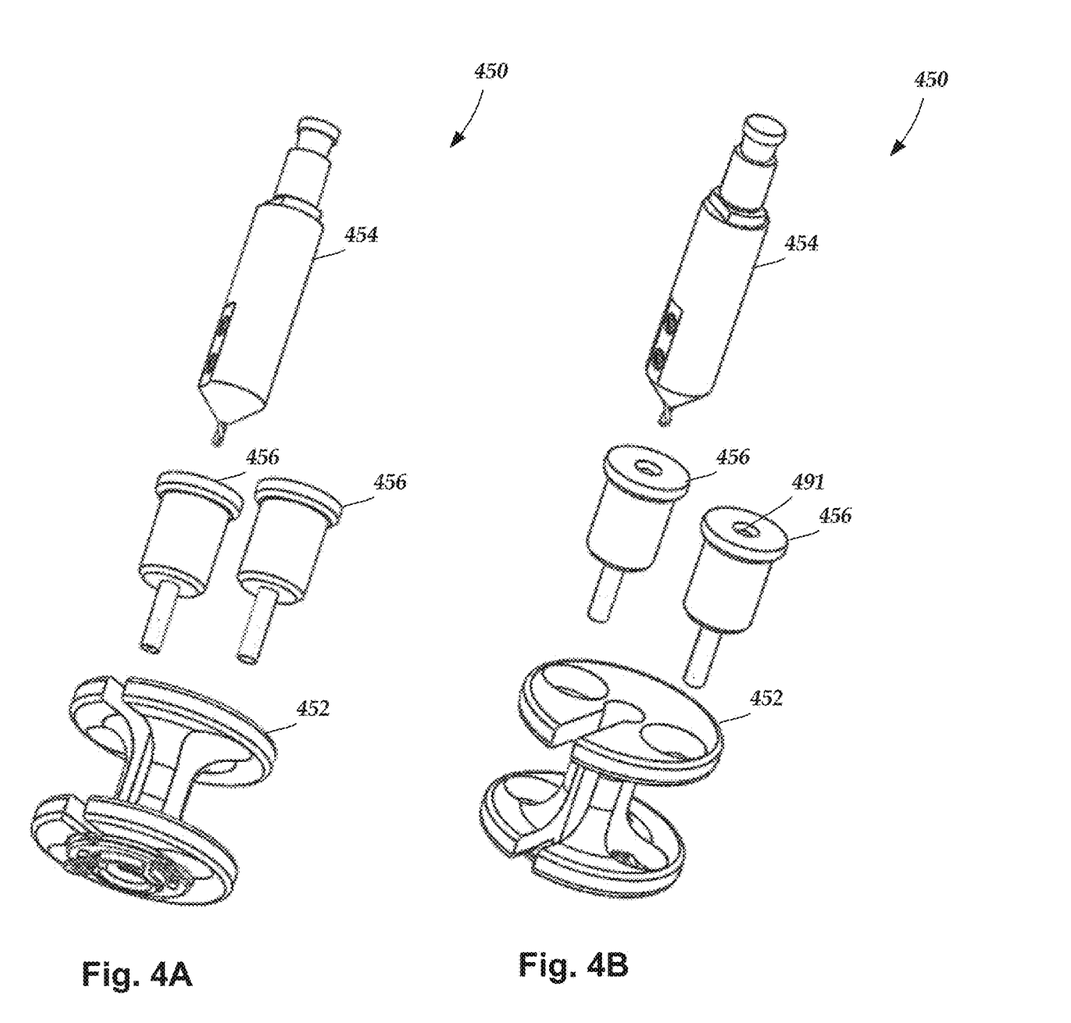
FIG. 4A is a perspective, exploded view of elements of one embodiment of a kit or arrangement for securing a burr hole plug to a skull of a patient.
FIG. 4B is a perspective, exploded view of the kit or arrangement of FIG. 4A from another perspective.

Accordingly, it is desirable to provide a methodology and tools for reliable placement, securement, and fixation of the burr hole plug to the patient's skull. FIGS. 4A and 4B illustrate one embodiment of a kit 450 or arrangement for placement, securement, and fixation of a burr hole plug to a patient's skull. The kit 450 includes a guide base 452, a drill shank 454, and one or more guide collets 456. Other kits may include more or fewer components than kit 450 illustrated in FIGS. 4A and 4B. Optionally, the kit 450 may also include a base 470 (FIG. 6A) for the burr hole plug. In other embodiments, the base 470 may be obtained from a separate burr hole plug. In yet other embodiments, the kit 450 may also include the complete burr hole plug arrangement. Examples of burr hole plugs can be found at U.S. Pat. Nos. 7,479,146; 8,043,304; 8,137,362; 8,425,534; 8,731,686; 8,764,767; 8,812,133; 9,043,000; and 9,050,191; and U.S. Patent Application Publications Nos. 2012/0316628 and 2013/0066430, all of which are incorporated herein by reference. It will be understood that other burr hole plugs may also be used with kit 450.

The kit 450 includes the guide base 452 and the drill shank 454 for pre-drilling pilot holes for the mounting fasteners of the burr hole plug. The one or more guide collets 456, in cooperation with the guide base 452, facilitate insertion and securement of the mounting fasteners to the skull.

Figure 5A:
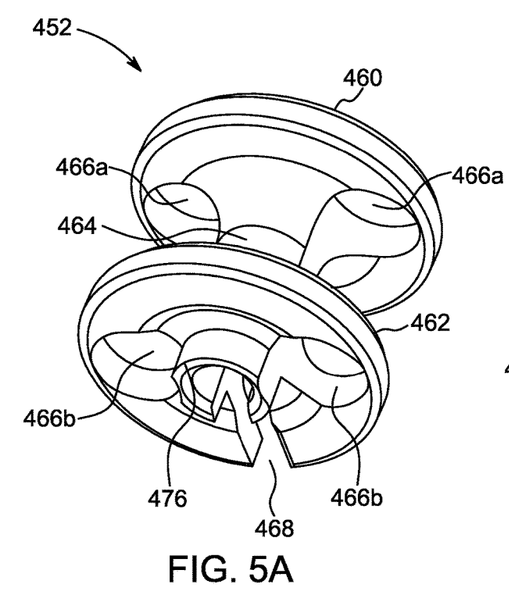
FIG. 5A is perspective view of one embodiment of a guide base of the kit or arrangement of FIG. 4A.
Figure 5B:
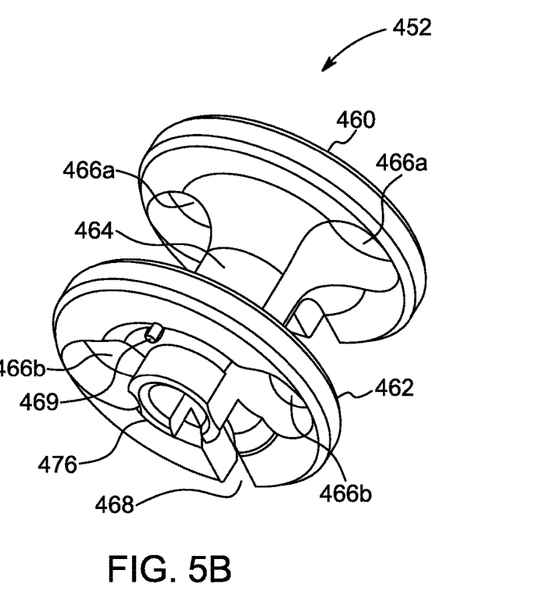
FIG. 5B is perspective view of another embodiment of a guide base of the kit or arrangement of FIG. 4A.
Figure 5C:
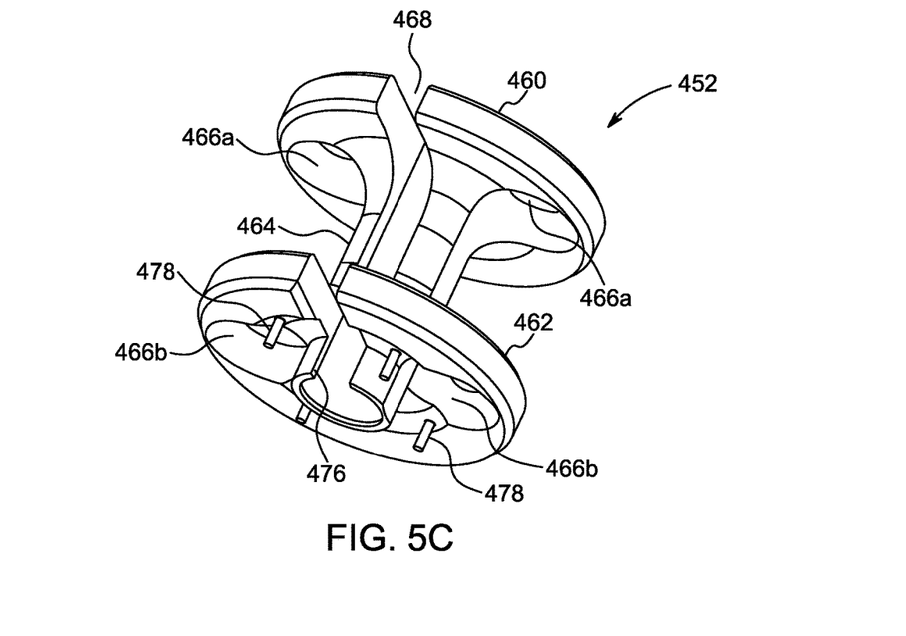
FIG. 5C is perspective view of a third embodiment of a guide base of the kit or arrangement of FIG. 4A.

FIGS. 5A, 5B, and 5C illustrate three embodiments of the guide base 452. The guide base 452 can be made of metal, rigid plastic, or any other suitable material, or any combination thereof. The guide base 452 includes an upper flange 460, a lower flange 462, and a connecting member 464 coupling the upper and lower flanges. Both the upper and lower flanges 460, 462 define one or more guide holes 466a, 466b for guiding the drill shank 454 and the guide collets 456. In the illustrated embodiments, each of the upper and lower flanges 460, 462 of the guide base 452 has two guide holes 466a, 466b because two fasteners are used to attach the burr hole plug to the skull. The guide holes 466a of the upper flange 460 are aligned with the guide holes 466b of the lower flange 462. It will be understood that other guide bases may have a different number of guide holes including, but not limited to, one, three, or four guide holes. In at least some embodiments, each of the upper and lower flanges 460, 462 of the guide base 452 has a number of guide holes 466a, 466b equal to a number of screws or other fasteners that will be used to secure the burr hole plug to the skull of the patient.

In at least some embodiments, the connecting member 464 is hollow to provide access or viewing through the burr hole. The guide base 452 also optionally defines a gap 468 extending into at least the lower flange 462 and may also extend into the upper flange 460 or the connecting member 464 (or any combination thereof) as shown in the illustrated embodiments. In at least some embodiments, the guide base 452 is used after implantation of the lead and the portion of the implanted lead which exits the burr hole can be inserted into or through, and remain positioned within, the gap 468 during use of the guide base 452.

Figure 6A:
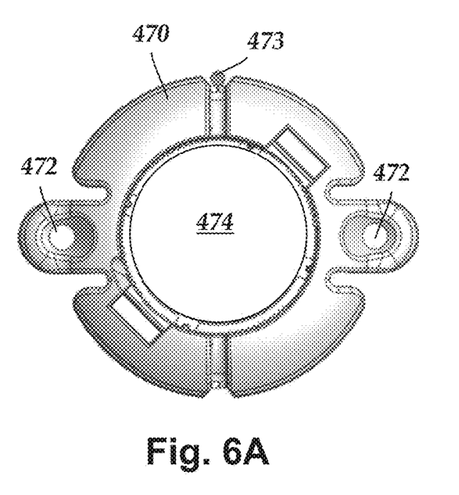
FIG. 6A is a top view of a base of burr hole plug.
Figure 6B:
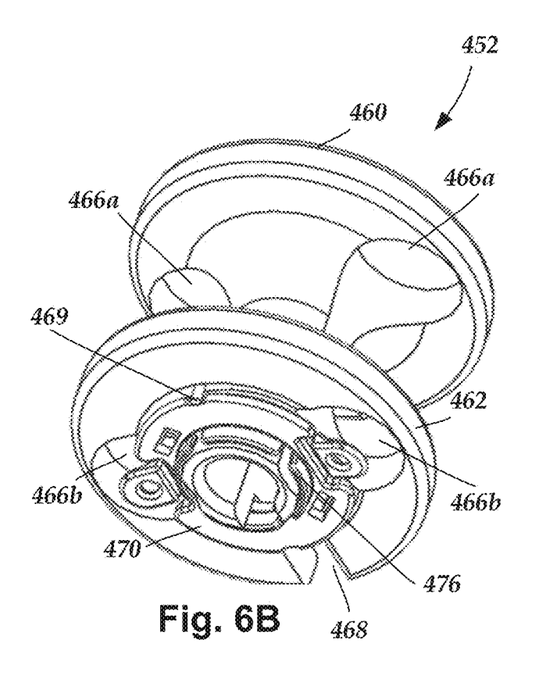
FIG. 6B is perspective view of the guide base of FIG. 5B with the base of the burr hole plug of FIG. 6A attached.

In at least some embodiments, the guide base 452 includes an alignment arrangement for aligning, and optionally attaching or fixing, the guide base to a base of a burr hole plug. FIG. 6A illustrates one embodiment of a base 470 of a burr hole plug including one or more fastener receiving opening 472, an optional alignment pin opening 473, and a burr hole opening 474. In FIG. 5A, the alignment arrangement on the guide base 452 takes the form of one or more sections 476 (for example, one or more curved walls) of a ring that extend from the lower flange 462. The one or more sections 476 fit into the burr hole opening 474 of the base 470 of the burr hole plug to align the base 470 with the guide base 452, as illustrated in FIG. 6B. In at least some embodiments, the sections 476 form a friction fit or a compression fit with the base to hold the base 470 on the guide base 452. As also illustrated in FIG. 6B, the fastener receiving openings 472 of the base 470 of the burr hole plug are aligned with the one or more guide holes 466b of the lower flange 462 of the guide base 452.

In FIG. 5B, the alignment arrangement on the guide base 452 includes the one or more section 476 of a ring and an alignment pin 469. The alignment pin 469 can be inserted into the alignment opening 473 (FIG. 6A) on the base 470. It will be understood that in other embodiments the alignment pin 469 can be on the base 470 and the alignment opening 473 can be on the guide base 452

In FIG. 5C, the alignment arrangement on the guide base 452 includes multiple pins 478 that can fit in corresponding holes, slots, or other elements of the base 470 of the burr hole plug. It will be understood that any other suitable alignment arrangement or combination of alignment arrangements can be used. For example, in FIG. 5C, the guide base 452 includes pins 478 and sections 476 of a ring that fit into the burr hole opening 474 of the base 470 of the burr hole plug. In addition, one of the pins 478 can serve the same function as the alignment pin 469 of FIG. 5B.

Figure 7A:
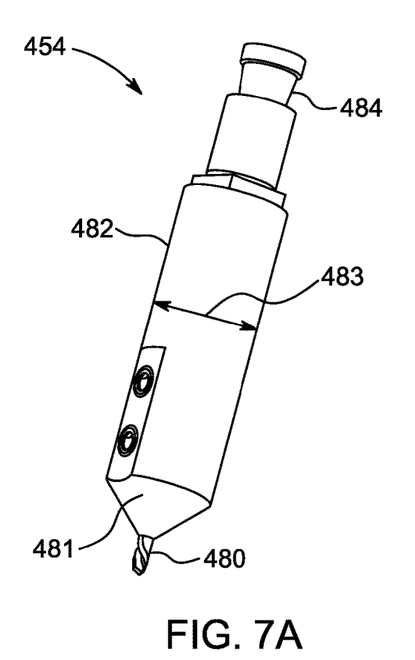
FIG. 7A is perspective view of one embodiment of a drill shank of the kit or arrangement of FIG. 4A.

FIG. 7A illustrates one embodiment of a drill shank 454 that includes a cutting element 480, a main shaft 482, and a drill engagement region 484. In at least some embodiments, the main shaft 482 has a sloping section 481 that leads to the cutting element 480. The drill shank 454 is typically made of metal but may also include other hard substances to facilitate drilling into the skull of the patient.

Figure 7B:
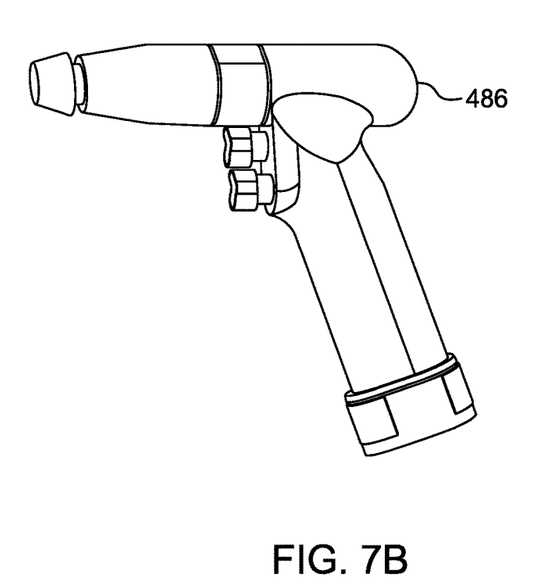
FIG. 7B is a side view of one embodiment of a drill for use with the drill shank of FIG. 7A.

The drill engagement region 484 is configured to fit and lock into a drill 486, illustrated in FIG. 7B. The drill engagement region 484 can have any suitable arrangement and may be dependent on the drill 486 that is used. Any suitable drill 486, including surgical drills, can be used. The drill 486 may be part of the kit 450 or may be separate from the kit.

The cutting element 480 of the drill shank 454 is sized in diameter to produce pilot holes for the screws (or other fasteners) of the burr hole plug. For example, the outer diameter of the cutting element 480 may be equal to or smaller than the outer diameter of the fasteners that will be used.

The main shaft 482 of the drill shank 454 has an outer diameter 483 that is smaller than the inner diameter of the guide hole 466a of the upper flange 460 of the guide base 452. The main shaft 482 of the drill shank 454 can be inserted through the guide hole 466a of the upper flange 460 in order to drill a pilot hole in the skull of the patient. The upper flange 460 provides a guide for the drill shank 454 to reliably drill the pilot hole at the desired position on the skull.

The guide hole 466b in the lower flange 462 of the guide base 452 also provides a guide for the drill shank 454. In addition, in at least some embodiments, the guide hole 466b and lower flange 462 may act as a stop for the drill shank 454 to limit the depth of the pilot hole or to prevent or hinder drilling too deeply into the skull of the patient. In at least some embodiments, the guide hole 466b of the lower flange 462 has an inner diameter that is less than the outer diameter 483 of the main shaft 482 of the drill shank 454 so that the main shaft 482 (or at least the non-sloping portion of the main shaft) is stopped at the lower flange 462.

Alternatively, the surface of the guide hole 466b may be sloping so that the inner diameter of the guide hole 466b decreases toward the portion of the guide base 452 that is positioned closest to the patient's skull. Along that sloping surface of the guide hole 466g the inner diameter of the guide hole 466b is smaller than the outer diameter 483 of the main shaft 482 (or at least the non-sloping portion of the main shaft) of the drill shank 454. In this alternative embodiment, the main shaft 482 (or the non-sloping portion of the main shaft) is stopped at some position along the guide hole 466b of the lower flange 462 of the guide base 452.

Figure 8:
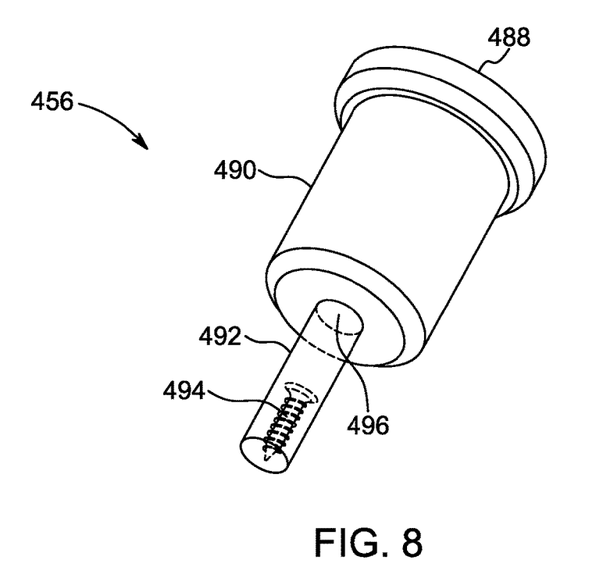
FIG. 8 is perspective view of one embodiment of a guide collet of the kit or arrangement of FIG. 4A.

FIG. 8 illustrates one embodiment of a guide collet 456 which includes a collet flange 488, a hollow collet shaft 490, a fastener tube 492, and, optionally, a fastener 494, such as a screw. In some embodiments, the fastener 494 is included with the guide collet 456 and, in other embodiments, the fastener is included with the burr hole plug and inserted into the guide collet 456 prior to use. There is an opening 496 through the bottom of the collet shaft 490 into the fastener tube 492 and a corresponding opening 491 (FIG. 4B) in the collet flange 488. The collet flange 488 and collet shaft 490 can be made of metal or rigid plastic. The fastener tube 492 can be made of flexible or rigid plastic or metal.

The collet flange 488 has an outer diameter that is greater than the outer diameter of the guide hole 466a of the upper flange 460. The collet shaft 490 has an outer diameter that is less than the outer diameter of the guide hole 466a of the upper flange 460. When the collet shaft 490 of the guide collet 456 is inserted into the guide hole 466a, the collet flange 488 rests on the upper flange 460. In some embodiments, the guide hole 466a of the upper flange 460 may be countersunk to enable the collet flange 488 to fit fully or partially within an upper portion of the guide hole 466a.

Preferably, the length of the collet shaft 490 and fastener tube 492 are selected so that the distal portion of the fastener tube 492 is disposed within the guide hole 466b of the lower flange 462 when the guide collet 456 is inserted into the guide base 452. The fastener tube 492 and openings in the collet flange 488 and collet shaft 490 are selected so that a tool such as a screwdriver (preferably, a torque limiting screwdriver) or other appropriate tool can be inserted through the collet flange, collet shaft, and fastener tube and engage the fastener to drive the fastener into the skull and secure the base 470 of the burr hole plug.

Figure 9A:
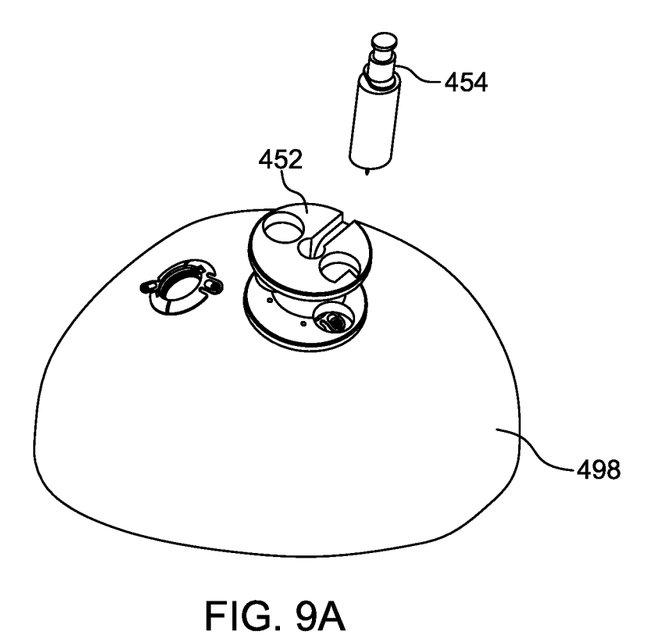
FIG. 9A is perspective view illustrating use of the guide base and drill shank of the kit or arrangement of FIG. 4A.
Figure 9B:
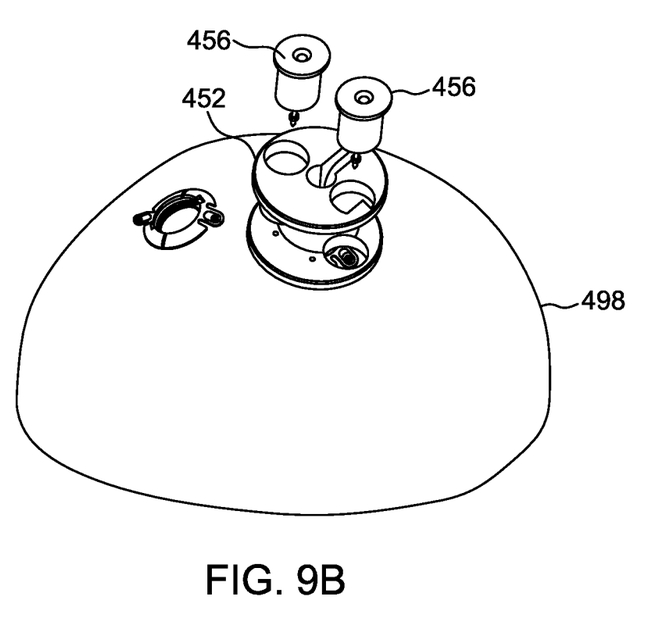
FIG. 9B is perspective view illustrating use of the guide base and guide collet of the kit or arrangement of FIG. 4A.
Figure 9C:
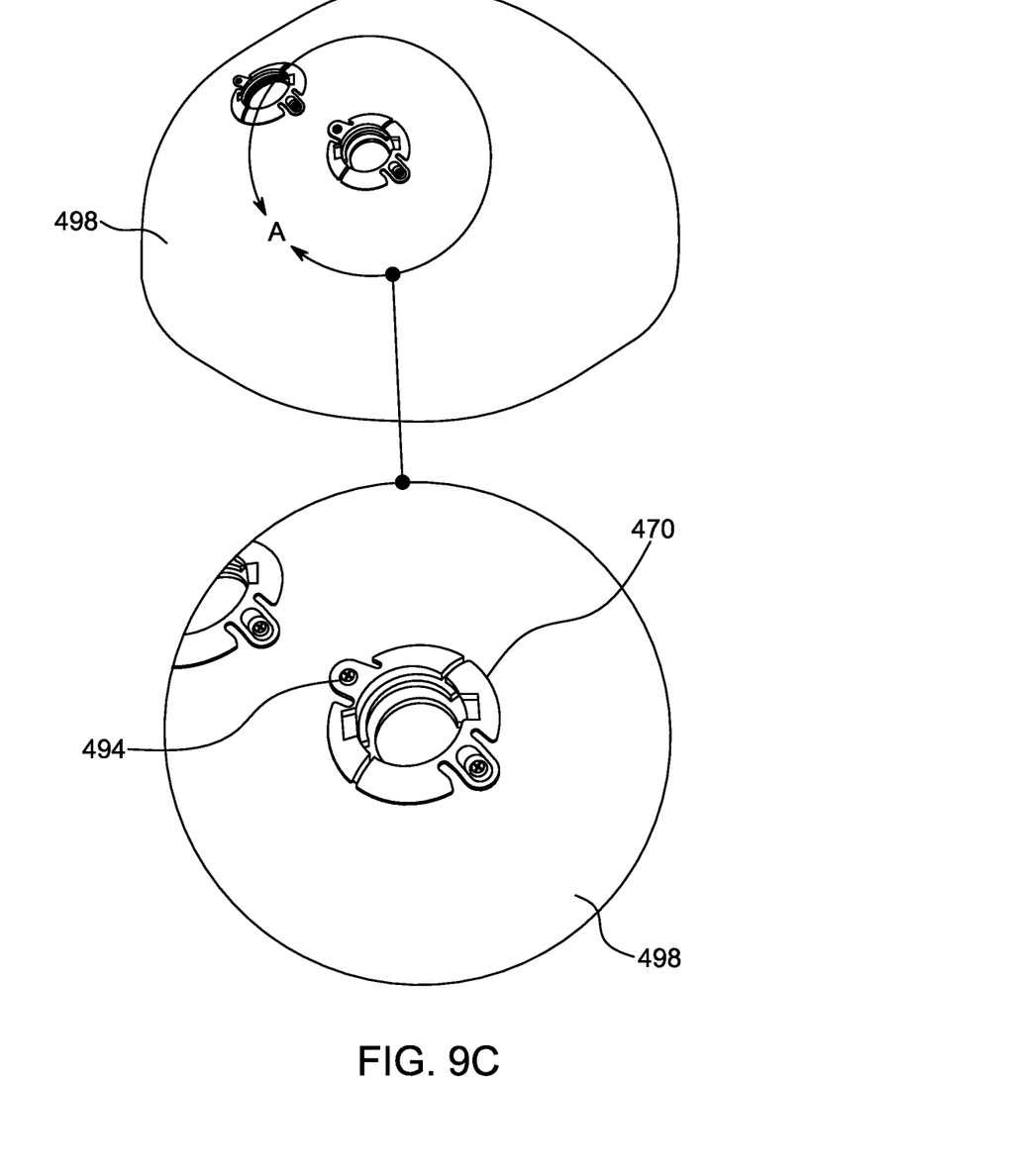
FIG. 9C is perspective view illustrating the base of a burr hole plug attached to a skull using the kit or arrangement of FIG. 4A.

FIGS. 9A-9C illustrate the use of the components of the kit. In FIG. 9A, the guide base 452 and the base 470 (FIG. 9C) of the burr hole plug are placed over the burr hole formed in the skull 498 of a patient. The drill shank 454 is attached to a drill (not shown) and then sequentially inserted into each of the guide holes 466a of the guide base 452 to drill a pilot hole in the skull. In FIG. 9B, the guide collets 456, with associated fasteners 494 (FIG. 9C), are inserted into the guide holes 466a of the guide base 452 and the fasteners are then driven into the skull using the drilled pilot holes. In FIG. 9C, the guide base 452 is removed leaving the base 470 of the burr hole plug attached to the skull 498 with the fasteners 494.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A kit for securing a burr hole plug, the kit comprising:
    a guide base comprising an upper flange, a lower flange, and a connecting member coupling the upper flange to the lower flange, each of the upper flange and the lower flange defining one or more guide holes, wherein the one or more guide holes of the upper flange are aligned with the one or more guide holes of the lower flange;
    a drill shank coupleable to a drill and comprising a cutting element and a main shaft that are configured to pass through any one of the one or more guide holes in the upper flange of the guide base; and
    one or more guide collets comprising a collet shaft and a fastener tube extending from the collet shaft and configured to receive a fastener, wherein the collet shaft and fastener tube are configured for insertion into any one of the one or more guide holes in the upper flange of the guide base.

2. The kit of claim 1, wherein each of the upper flange and the lower flange defines at least two of the guide holes.

3. The kit of claim 1, wherein the main shaft of the drill shank has an outer diameter that is greater than an inner diameter of any one of the one or more guide holes in the lower flange of the guide base.

4. The kit of claim 1, wherein each of the one or more guide holes in the lower flange has a diameter that decreases toward a bottom of the lower flange, wherein the main shaft of the drill shank has an outer diameter that is greater than an inner diameter of at least a portion of any one of the one or more guide holes in the lower flange of the guide base.

5. The kit of claim 1, wherein the one or more guide collets each comprise a collet flange disposed on the collet shaft opposite the fastener tube.

6. The kit of claim 5, wherein the one or more guide collets each have an outer diameter larger than an inner diameter of any one of the one or more guide holes in the upper flange of the guide base.

7. The kit of claim 1, wherein the guide base further comprises an alignment arrangement extending from the lower flange to align a base of the burr hole plug with the one or more guide holes of the upper and lower flanges.

8. The kit of claim 7, wherein the alignment arrangement comprises one or more sections of a ring that fit within an opening of the base of the burr hole plug.

9. The kit of claim 8, wherein the one or more sections of the ring form a compression or friction fit with the base of the burr hole plug.

10. The kit of claim 7, wherein the alignment arrangement comprises one or more pins for engaging the base of the burr hole plug.

11. The kit of claim 7, further comprising the base of the burr hole plug.

12. The kit of claim 1, further comprising one or more fasteners with each fastener disposed in the fastener tube of one of the one or more guide collets.

13. The kit of claim 1, further comprising the burr hole plug.

14. The kit of claim 1, wherein the guide base defines a gap in at least the lower flange for positioning of a lead extending from a burr hole.

15. The kit of claim 14, wherein the guide base further defines the gap in the upper flange and the connecting member.

16. A method of securing a burr hole plug to a patient using the kit of claim 1, the method comprising:

aligning the guide base with a base of a burr hole plug on a skull of a patient, wherein the one or more guide holes of the upper and lower flanges are aligned with fastener openings in the base of the burr hole plug;

drilling one or more pilot holes in the skull using the drill shank inserted into the one or more guide holes of the guide base;

inserting the one or more guide collets into the guide holes of the guide base with a fastener in the fastener tube of each of the one or more guide collets;

driving the one or more fasteners into the skull using the guide collets and the one or more pilot holes; and removing the guide base leaving the base of the burr hole plug secured to the skull.

17. The method of claim 16, wherein aligning the guide base comprises engaging the base of the burr hole plug with an alignment arrangement extending from the lower flange of the guide base.

18. The method of claim 17, wherein engaging the base of the burr hole plug comprises forming a compression or friction fit between the alignment arrangement of the guide base and the base of the burr hole plug.

19. The method of claim 17, wherein the alignment arrangement comprises one or more pins and engaging the base of the burr hole plug comprises engaging the base of the burr hole plug with the one or more pins of the alignment arrangement of the guide base.

20. The method of claim 16, wherein aligning the guide base comprises positioning a lead extending from a burr hole in a gap defined in at least the lower flange of the guide base.

* * * * *